(12) United States Patent
Morita

(10) Patent No.: US 11,083,410 B2
(45) Date of Patent: Aug. 10, 2021

(54) MAMMARY GLAND CONTENT RATE CALCULATION DEVICE, METHOD, AND PROGRAM

(71) Applicant: FUJIFILM CORPORATION, Tokyo (JP)

(72) Inventor: Junya Morita, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 341 days.

(21) Appl. No.: 16/027,384

(22) Filed: Jul. 5, 2018

(65) Prior Publication Data

US 2019/0069834 A1 Mar. 7, 2019

(30) Foreign Application Priority Data

Sep. 7, 2017 (JP) .............................. JP2017-172318

(51) Int. Cl.
| | |
|---|---|
| *A61B 5/05* | (2021.01) |
| *A61B 5/00* | (2006.01) |
| *G06T 7/00* | (2017.01) |
| *G06T 7/62* | (2017.01) |
| *A61B 6/00* | (2006.01) |

(52) U.S. Cl.
CPC .......... *A61B 5/4288* (2013.01); *G06T 7/0012* (2013.01); *G06T 7/62* (2017.01); *A61B 6/502* (2013.01); *A61B 6/5217* (2013.01); *G06T 2207/10116* (2013.01); *G06T 2207/30068* (2013.01)

(58) Field of Classification Search
None
See application file for complete search history.

(56) References Cited

U.S. PATENT DOCUMENTS

| | | | | |
|---|---|---|---|---|
| 2007/0201617 A1* | 8/2007 | Nakayama | ............. | A61B 6/544 378/108 |
| 2010/0246924 A1* | 9/2010 | Morita | ................. | A61B 5/4872 382/132 |

FOREIGN PATENT DOCUMENTS

JP 2010-253245 A 11/2010

* cited by examiner

*Primary Examiner* — Joel F Brutus
(74) *Attorney, Agent, or Firm* — SOLARIS Intellectual Property Group, PLLC

(57) ABSTRACT

An image acquisition unit acquires a breast image, and a first estimation unit calculates a first estimated value of a direct arrival dose in a direct X-ray region, which is included in the breast image and to which X-rays are directly emitted, based on the imaging conditions at the time of X-ray imaging. A second estimation unit calculates a second estimated value of the direct arrival dose based on the pixel value of the direct X-ray region included in the breast image. A determination unit determines a direct arrival dose, which is used for calculation of the mammary gland content rate, based on the first estimated value and the second estimated value. A calculation unit calculates a mammary gland content rate using the direct arrival dose determined by the determination unit.

9 Claims, 4 Drawing Sheets

LUT1

| W/Rh | |
|---|---|
| 22kV | 1.58 |
| ⋮ | |
| 28kV | 3.98 |
| ⋮ | |
| 35kV | 6.68 |
| ⋮ | |

LUT2

| W/Rh | |
|---|---|
| 22kV | 59.0 |
| ⋮ | |
| 28kV | 86.7 |
| ⋮ | |
| 35kV | 109.5 |
| ⋮ | |

MAMMARY GLAND CONTENT RATE CALCULATION DEVICE, METHOD, AND PROGRAM

CROSS REFERENCE TO RELATED APPLICATIONS

The present application claims priority under 35 U.S.C. § 119 to Japanese Patent Application No. 2017-172318 filed on Sep. 7, 2017. The above application is hereby expressly incorporated by reference, in its entirety, into the present application.

BACKGROUND

Field of the Invention

The present invention relates to a mammary gland content rate calculation device, method, and program for calculating the mammary gland content rate of a breast using a breast image obtained by imaging the breast with X-rays.

Related Art

In recent years, in order to encourage the early detection of breast cancer, image diagnosis using a radiographic image capturing apparatus (called mammography) for imaging a breast has been drawing attention. In mammography, the breast is placed on an imaging table, and imaging is performed in a state in which the breast is compressed by a compression plate. The breast is mainly formed of mammary gland tissues and adipose tissues, and it is important for diagnosis to find a lesion hidden in the mammary gland tissue. For this reason, a radiographic image (breast image) of the breast imaged by mammography is provided to a doctor for diagnosis after being subjected to image processing with a dedicated operation terminal or the like. The doctor examines the presence or absence of a lesion, such as a tumor and calcification, by displaying the breast image on a display and interpreting the breast image.

Here, the proportion of mammary gland in the breast is called a mammary gland content rate. The mammary gland content rate is very useful for accurately ascertaining the characteristics of the breast, and this is medically indispensable information. For example, research suggests that there is a correlation between the mammary gland content rate and the risk of carcinogenesis. For this reason, various methods for calculating the mammary gland content rate have been proposed. For example, JP2010-253245A proposes a method of calculating a mammary gland content rate from a breast image acquired by mammography. In the method described in JP2010-253245A, in mammography, the mammary gland content rate is calculated based on the relationship among the X-ray dose directly reaching a radiation detector without being transmitted through the breast as a subject, the X-ray dose reaching the radiation detector after being transmitted through the breast, an X-ray attenuation coefficient due to fat, an X-ray attenuation coefficient due to mammary gland, and the thickness of the breast.

As the X-ray dose (hereinafter, referred to as a direct arrival dose) directly reaching a radiation detection panel without being transmitted through the breast, a pixel value of a direct X-ray region, which is obtained by directly emitting X-rays to the radiation detector, in the breast image is used. However, in a case where the imaging dose is large, a signal output in the direct X-ray region may exceed the dynamic range of the radiation detector, and the pixel value may be saturated. In a case where the pixel value is saturated in this manner, it is not possible to accurately calculate the mammary gland content rate. For this reason, it is conceivable to estimate the direct arrival dose from the imaging conditions. The arrival dose to the radiation detection panel and the acquired pixel value have a proportional relationship therebetween. Therefore, for example, it is conceivable to calculate the direct arrival dose from the pixel value of the direct X-ray region based on an X-ray dose (mAs value) at the time of imaging, a dose rate (mR/mAs), and panel sensitivity (QL/mR) that is the sensitivity of the radiation detector.

However, the X-ray tube used in mammography deteriorates with time, and the sensitivity of the radiation detector also changes with time. In a case where the deterioration of the X-ray tube and the change in the sensitivity of the radiation detector occur as described above, the relationship between the imaging conditions and the direct arrival dose changes. Therefore, even in a case where the direct arrival dose calculated based on the imaging conditions is used, it is not possible to accurately calculate the mammary gland content rate.

SUMMARY

The invention has been made in view of the above circumstances, and it is an object of the invention to accurately calculate a mammary gland content rate regardless of saturation of a pixel value in a breast image and changes in imaging conditions at the time of imaging a breast.

A mammary gland content rate calculation device according to the invention comprises: an image acquisition unit that acquires a breast image obtained by imaging a breast with X-rays; a first estimation unit that calculates a first estimated value of a direct arrival dose in a direct X-ray region, which is included in the breast image and to which X-rays are directly emitted, based on imaging conditions at the time of the X-ray imaging; a second estimation unit that calculates a second estimated value of the direct arrival dose based on a pixel value of the direct X-ray region included in the breast image; a determination unit that determines a direct arrival dose, which is to be used for calculation of a mammary gland content rate, based on the first estimated value and the second estimated value; and a calculation unit that calculates the mammary gland content rate of the breast based on a breast region arrival dose, which is an arrival dose of X-rays to a region of the breast included in the breast image, and the determined direct arrival dose.

In the mammary gland content rate calculation device according to the invention, the determination unit may determine whether or not a maximum value of the pixel value of the direct X-ray region included in the breast image is saturated, and calculate a ratio between the first estimated value and the second estimated value as a correction coefficient of the first estimated value in a case where it is determined that the maximum value is not saturated. The determination regarding whether or not the maximum value of the pixel value is saturated may be performed by determining whether or not the maximum value is a maximum value that the pixel value of the breast image can take, or may be performed by determining whether or not the maximum value is equal to or greater than a predetermined threshold value.

In the mammary gland content rate calculation device according to the invention, the determination unit may correct the first estimated value with the correction coefficient, and determine the corrected first estimated value as a direct arrival dose to be used for calculation of the mammary gland content rate.

The mammary gland content rate calculation device according to the invention may further comprise a storage unit that stores the correction coefficient. The determination unit may calculate a representative value of a predetermined number of correction coefficients stored in the storage unit, correct the first estimated value with the representative value, and determine the corrected first estimated value as a direct arrival dose to be used for calculation of the mammary gland content rate.

The "representative value" is a statistical value representing a predetermined number of correction coefficients, and any value can be adopted. For example, an average value, a median value, a mode value, a maximum value, or a minimum value of a predetermined number of correction coefficients can be used as a representative value.

In the mammary gland content rate calculation device according to the invention, the determination unit may determine whether or not a maximum value of the pixel value of the direct X-ray region included in the breast image is saturated, and determine the first estimated value as a direct arrival dose to be used for calculation of the mammary gland content rate in a case where it is determined that the maximum value is saturated and determine the second estimated value as a direct arrival dose to be used for calculation of the mammary gland content rate in a case where it is determined that the maximum value is not saturated.

In the mammary gland content rate calculation device according to the invention, the first estimation unit may acquire a dose rate and a sensitivity of a radiation detector, which is for acquiring the breast image, based on the imaging conditions, and calculate the first estimated value using an X-ray dose at the time of the X-ray imaging, the dose rate, and the sensitivity of the radiation detector.

In the mammary gland content rate calculation device according to the invention, for each type of target/filter and a tube voltage in an X-ray source used at the time of the X-ray imaging, the first estimation unit may acquire the dose rate and the sensitivity of the radiation detector with reference to a table in which values of the dose rate and the sensitivity of the radiation detector are set.

A mammary gland content rate calculation method according to the invention comprises: acquiring a breast image obtained by imaging a breast with X-rays; calculating a first estimated value of a direct arrival dose in a direct X-ray region, which is included in the breast image and to which X-rays are directly emitted, based on imaging conditions at the time of the X-ray imaging; calculating a second estimated value of the direct arrival dose based on a pixel value of the direct X-ray region included in the breast image; determining a direct arrival dose, which is to be used for calculation of a mammary gland content rate, based on the first estimated value and the second estimated value; and calculating the mammary gland content rate of the breast based on a breast region arrival dose, which is an arrival dose of X-rays to a region of the breast included in the breast image, and the determined direct arrival dose.

In addition, a program causing a computer to execute the mammary gland content rate calculation method according to the invention may be provided.

Another mammary gland content rate calculation device according to the invention comprises: a memory that stores commands to be executed by a computer; and a processor configured to execute the stored commands. The processor is configured to execute processing for acquiring a breast image obtained by imaging a breast with X-rays; processing for calculating a first estimated value of a direct arrival dose in a direct X-ray region, which is included in the breast image and to which X-rays are directly emitted, based on imaging conditions at the time of the X-ray imaging; processing for calculating a second estimated value of the direct arrival dose based on a pixel value of the direct X-ray region included in the breast image; processing for determining a direct arrival dose, which is to be used for calculation of a mammary gland content rate, based on the first estimated value and the second estimated value; and processing for calculating the mammary gland content rate of the breast based on a breast region arrival dose, which is an arrival dose of X-rays to a region of the breast included in the breast image, and the determined direct arrival dose.

According to the invention, the first estimated value of the direct arrival dose in the direct X-ray region of the breast image is calculated based on the imaging conditions at the time of X-ray imaging, and the second estimated value of the direct arrival dose is calculated based on the pixel value in the direct X-ray region of the breast image. Then, the direct arrival dose used for calculation of the mammary gland content rate is determined based on the first estimated value and the second estimated value, and the mammary gland content rate of the breast is calculated based on the breast region arrival dose, which is an arrival dose to the region of the breast included in the breast image, and the determined direct arrival dose. Therefore, by selecting an estimated value to be used or correcting the estimated value according to the case where the pixel value is saturated in the breast image and the case where the imaging conditions at the time of imaging are changed, it is possible to determine the direct arrival dose to be used for calculation of the mammary gland content rate. As a result, it is possible to accurately calculate the mammary gland content rate regardless of saturation of the pixel value in the breast image and changes in the imaging conditions at the time of imaging the breast.

DETAILED DESCRIPTION

Figure 1:
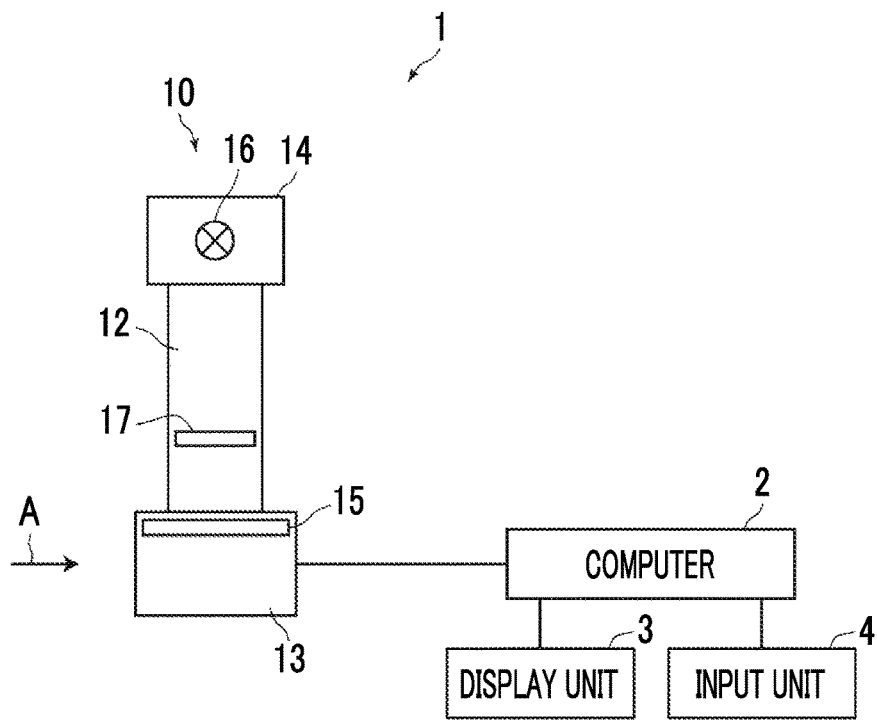
FIG. 1 is a schematic configuration diagram of a radiographic image capturing apparatus to which a mammary gland content rate calculation device according to an embodiment of the invention is applied.
Figure 2:
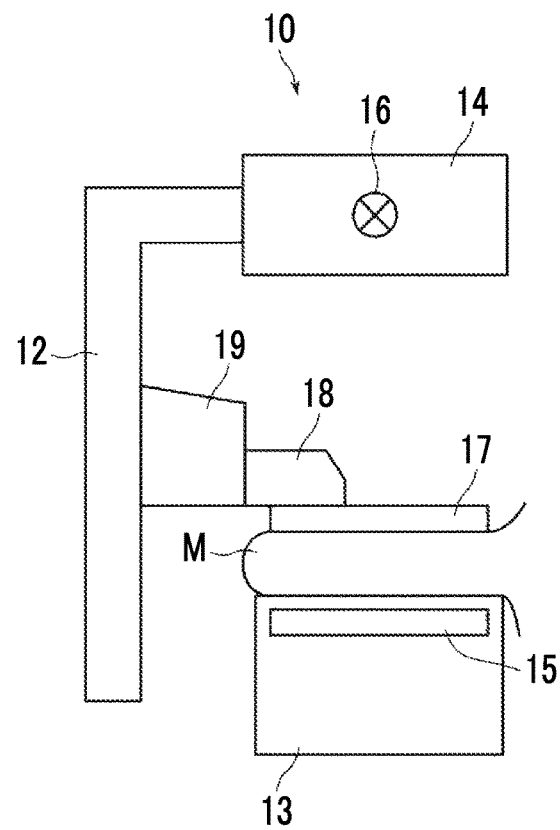
FIG. 2 is a diagram of the radiographic image capturing apparatus as viewed from the direction of arrow A in FIG. 1.

Hereinafter, an embodiment of the invention will be described with reference to the accompanying diagrams. FIG. 1 is a schematic configuration diagram of a radiographic image capturing apparatus to which a mammary gland content rate calculation device according to a first embodiment of the invention is applied, and FIG. 2 is a diagram of the radiographic image capturing apparatus as viewed from the direction of arrow A in FIG. 1. A radiographic image capturing apparatus 1 is a mammography apparatus that captures an image of a breast M that is a subject. As shown in FIG. 1, the radiographic image capturing apparatus 1 includes an imaging unit 10, a computer 2 connected to the imaging unit 10, and a display unit 3 and an input unit 4 connected to the computer 2.

The imaging unit 10 includes an arm unit 12. An imaging table 13 is attached to one end portion of the arm unit 12, and an irradiation unit 14 is attached to the other end portion so as to face the imaging table 13.

A radiation detector 15, such as a flat panel detector, is provided inside the imaging table 13. In addition, a circuit board on which a charge amplifier for converting a charge signal read from the radiation detector 15 into a voltage signal, a sampling two correlation pile circuit for sampling a voltage signal output from the charge amplifier, an AD conversion unit for converting a voltage signal into a digital signal, and the like are provided is provided inside the imaging table 13.

The radiation detector 15 can perform recording and reading of a radiographic image repeatedly. A so-called direct type radiation detector that generates an electric charge by direct reception of radiation may be used, or a so-called indirect type radiation detector that converts radiation into visible light and then converts the visible light into a charge signal may be used. As a method of reading a radiographic image signal, it is desirable to use a so-called TFT reading method in which a radiographic image signal is read by ON and OFF of a thin film transistor (TFT) switch or a so-called optical reading method in which a radiographic image signal is read by emission of reading light. However, other methods may also be used without being limited to the above methods.

In the present embodiment, the radiation detector 15 has a unique sensitivity (hereinafter, referred to as a panel sensitivity) with respect to emitted X-rays. The panel sensitivity is expressed by the pixel value (QL) obtained per unit amount of the radiation dose (mR) to the radiation detector 15, that is, QL/mR.

An X-ray source 16, which is a radiation source, is housed inside the irradiation unit 14. The timing of emission of X-rays, which are radiations from the X-ray source 16, and X-ray generation conditions in the X-ray source 16, that is, imaging conditions such as a tube voltage and irradiation time, are controlled by the computer 2.

The X-ray source 16 includes a filament for outputting an electron beam, a target for generating X-rays by collision of an electron beam, and a filter for adjusting the energy spectrum of X-rays. The target has a plurality of different anode materials, for example, molybdenum (Mo), rhodium (Rh), and tungsten (W), and these are disposed so as to be selectable. The filter has a plurality of different materials, for example Mo, Rh, W, and aluminum (Al), and these are disposed so as to be selectable.

The imaging conditions are conditions for obtaining an appropriate radiographic image by adjusting the energy spectrum (line quality) of X-rays emitted to the breast M. For example, the imaging conditions include a combination of the target and the filter that form the X-ray source 16, a tube voltage (kV), and an mAs value (tube current×irradiation time).

In the present embodiment, the radiographic image capturing apparatus 1 has a unique dose rate. The dose rate is expressed by the radiation dose (mR) obtained per unit amount of the X-ray dose (mAs value) emitted from the X-ray source 16, that is, mR/mAs.

A compression plate 17 disposed above the imaging table 13 in order to compress the breast M, a support unit 18 for supporting the compression plate 17, and a moving mechanism 19 for moving the support unit 18 in the vertical direction in FIGS. 1 and 2 are provided in the arm unit 12. Information of the distance between the compression plate 17 and the imaging table 13, that is, information of the height of the compression plate 17, is input to the computer 2.

The display unit 3 is a display device, such as a cathode ray tube (CRT) or a liquid crystal monitor, and displays a breast image that is an X-ray image of the breast M acquired as will be described later, a message required for the operation, and the like. The display unit 3 may include a speaker to output sound.

The input unit 4 is a keyboard, a mouse, or a touch panel type input device, and receives an operation on the radiographic image capturing apparatus 1 by the operator. In addition, the input unit 4 receives an input of various kinds of information, such as imaging conditions, and an instruction to modify the information, which are required to perform imaging. In the present embodiment, each unit of the radiographic image capturing apparatus 1 operates according to the information input from the input unit 4 by the operator.

A mammary gland content rate calculation program is installed on the computer 2. In the present embodiment, the computer may be a workstation or a personal computer that is directly operated by the operator, or may be a server computer connected to these through a network. The energy subtraction processing program is distributed by being recorded on a recording medium, such as a digital versatile disc (DVD) and a compact disc read only memory (CD-ROM), and is installed on the computer from the recording medium. Alternatively, the energy subtraction processing program is stored in a storage device of a server computer connected to the network or in a network storage so as to be accessible from the outside, and is downloaded and installed on the computer as necessary.

Figure 3:
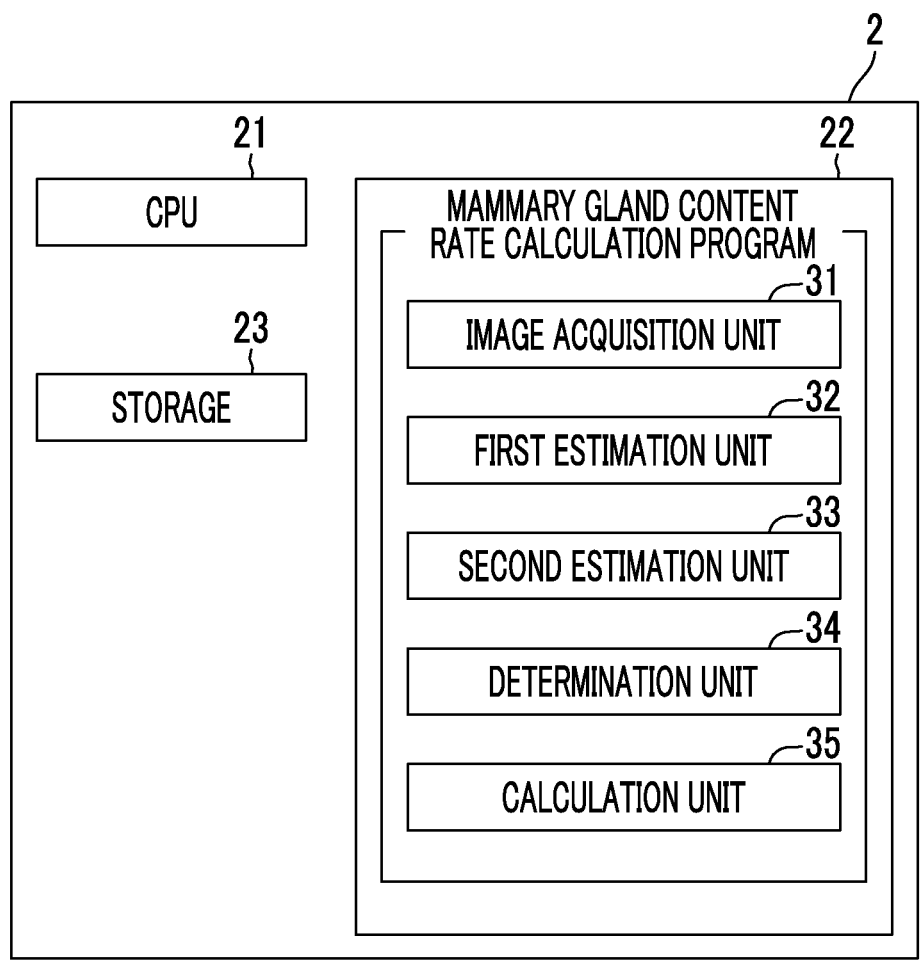
FIG. 3 is a diagram showing the schematic configuration of the mammary gland content rate calculation device according to the present embodiment.

FIG. 3 is a diagram showing the schematic configuration of a mammary gland content rate calculation device realized by installing a mammary gland content rate calculation program onto the computer 2. As shown in FIG. 3, the mammary gland content rate calculation device includes a central processing unit (CPU) 21, a memory 22, and a storage 23 as the configuration of a standard computer.

The storage 23 is a storage device, such as a hard disk or a solid state drive (SSD), and stores various kinds of information required for processing including a program for driving each unit of the radiographic image capturing apparatus 1 and a mammary gland content rate calculation program. A breast image acquired by imaging is also stored in the storage 23. Various tables to be described later are also stored in the storage 23. The storage 23 corresponds to a storage unit.

The memory 22 temporarily stores programs and the like stored in the storage 23 so that the CPU 21 executes various kinds of processing. As processing to be executed by the CPU 21, the mammary gland content rate calculation program defines: image acquisition processing for acquiring a breast image by causing the radiographic image capturing apparatus 1 to perform X-ray imaging; first estimation processing for calculating a first estimated value of a direct arrival dose in a direct X-ray region, which is included in the breast image and to which X-rays are directly emitted, based on imaging conditions at the time of X-ray imaging; second estimation processing for calculating a second estimated value of the direct arrival dose based on the pixel value of the direct X-ray region included in the breast image; determination processing for determining a direct arrival dose, which is to be used in calculating the mammary gland content rate, based on the first estimated value and the second estimated value; and calculation processing for calculating the mammary gland content rate of the breast M based on a breast region arrival dose, which is the arrival dose of X-rays to the breast region included in the breast image, and the determined direct arrival dose.

The CPU 21 executes these processes according to the mammary gland content rate calculation program, so that the computer 2 functions as an image acquisition unit 31, a first estimation unit 32, the second estimation unit 33, a determination unit 34, and a calculation unit 35. The computer 2 may include a processor or a processing circuit for performing each of the image acquisition processing, the first estimation processing, the second estimation processing, the determination processing, and the calculation processing.

The image acquisition unit 31 acquires a breast image G0 by controlling the irradiation unit 14 according to predetermined imaging conditions. Specifically, according to the predetermined imaging conditions, the target and the filter of the X-ray source 16 are set, and the tube voltage and the mAs value are set. Then, X-rays are emitted to the breast M by driving the X-ray source 16 according to the set imaging conditions, and X-rays transmitted through the breast M are detected by the radiation detector 15, thereby acquiring the breast image G0.

The first estimation unit 32 calculates a first estimated value I1 of the direct arrival dose in a direct X-ray region, which is included in the breast image G0 and to which X-rays are directly emitted, based on the imaging conditions at the time of X-ray imaging. Specifically, the dose rate at the time of X-ray imaging and the panel sensitivity of the radiation detector 15 are acquired based on the imaging conditions, and the first estimated value is calculated using the X-ray dose, the dose rate, and the panel sensitivity included in the imaging conditions. In the present embodiment, a table LUT1 in which the dose rate (mR/mAs) is set according to various target/filter types and tube voltages in the X-ray source 16 and a table LUT2 in which the panel sensitivity (QL/mR) is set according to various target/filter types and tube voltages in the X-ray source 16 are stored in the storage 23.

The table LUT1 is created by calibrating each apparatus. Specifically, a dosimeter is attached to the radiation detector 15, X-rays of a predetermined imaging dose are emitted to the radiation detector 15 while variously changing the target/filter and the tube voltage, and a radiation dose to the radiation detector 15 is detected by the dosimeter. Then, the dose rate is calculated by dividing the detected radiation dose by the imaging dose. Then, by storing the calculated dose rate so as to be associated with the target/filter and the tube voltage, the table LUT1 is created.

For the table LUT2, X-rays of a predetermined imaging dose are emitted to the radiation detector 15 while variously changing the target/filter and the tube voltage, and a radiation dose is detected by the dosimeter and the signal value (QL) output from the radiation detector 15 is detected. Then, the panel sensitivity is calculated by dividing the detected signal value by the radiation dose. Then, by storing the calculated panel sensitivity so as to be associated with the target/filter and the tube voltage, the table LUT2 is created.

Figures 4, 5:
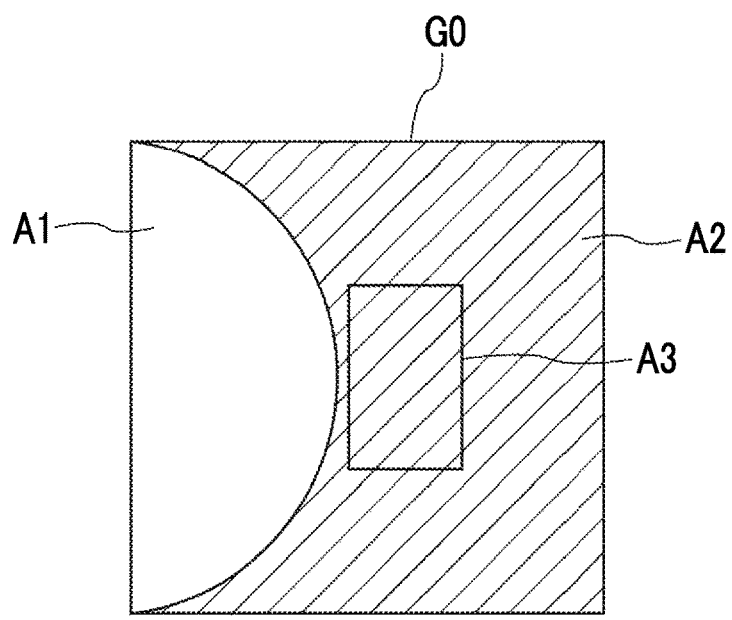
FIG. 4 is a diagram showing tables of a dose rate and panel sensitivity.
FIG. 5 is a diagram illustrating division of a breast image into a breast region and a direct X-ray region.

FIG. 4 is a diagram showing examples of the tables LUT1 and LUT2. As shown in FIG. 4, various tube voltages and dose rates are associated with the table LUT1 according to the type of target/filter. In addition, various tube voltages and panel sensitivities are associated with the table LUT2 according to the type of target/filter. By referring to the tables LUT1 and LUT2 shown in FIG. 4, in a case where the target/filter is W/Rh and the tube voltage is 28 kV, the dose rate of 3.98 mR/mAs and the panel sensitivity of 86.7 QL/mR are acquired. In FIG. 4, only the values in a case where the target/filter is W/Rh are shown for the sake of description. However, dose rates and panel sensitivities for various target/filter types are set in the tables LUT1 and LUT2.

Based on the target/filter type and the tube voltage included in the imaging conditions, the first estimation unit 32 acquires the dose rate with reference to the table LUT1 and acquires the panel sensitivity with reference to the table LUT2. Then, the first estimation unit 32 calculates the first estimated value I1 by the following Equation (1).

$$I1 = \text{X-ray dose (mAs)} \times \text{dose rate (mR/mAs)} \times \text{panel sensitivity (QL/mR)} \quad (1)$$

The second estimation unit 33 calculates a second estimated value I2 of the direct arrival dose based on the pixel value of the direct X-ray region included in the breast image G0. For this reason, the second estimation unit 33 divides the breast image G0 into a breast region and a direct X-ray region. FIG. 5 is a diagram illustrating division of a breast image into a breast region and a direct X-ray region. Since the direct X-ray region shows a particularly high density on the breast image G0, a peak appearing on the high density side in the density histogram of the entire image corresponds to the direct X-ray region. The second estimation unit 33 calculates the density histogram of the breast image G0 and performs binarization processing with a value, which is obtained by subtracting a predetermined value from the peak value on the high density side of the density histogram, as a threshold value, thereby dividing the breast image G0 into a breast region A1 and a direct X-ray region A2. Alternatively, searching may be performed from the high density side in the density histogram, and the binarization processing may be performed by using a point, of which a value becomes equal to or less than the predetermined value first, as a threshold value.

As shown in FIG. 5, the second estimation unit 33 sets a region corresponding to the vicinity of the center of the radiation detector 15, in the direct X-ray region A2 of the breast image G0, as an analysis region A3 for calculating the second estimated value I2. By setting the region corresponding to the vicinity of the center of the radiation detector 15 as the analysis region A3 in this manner, the influence of the variation of the pixel value in the detection plane of the radiation detector 15 on the calculation of a correction coefficient, which will be described later, can be reduced.

Then, the second estimation unit 33 calculates an average value of pixel values in the analysis region A3 as the second estimated value I2. In addition, the second estimation unit 33 calculates a maximum value Imax of pixel values in the analysis region A3.

The determination unit 34 determines a direct arrival dose Id, which is used for calculation of the mammary gland content rate, based on the first estimated value I1 and the second estimated value I2. Therefore, the determination unit 34 determines whether or not the maximum value Imax of the pixel values in the analysis region A3, which has been calculated by the second estimation unit 33, is saturated. The determination regarding whether or not the maximum value Imax is saturated is performed by determining whether or not the maximum value Imax is a maximum value of pixel values that the breast image G0 can take. Alternatively, the determination regarding whether or not the maximum value Imax is saturated may be performed by determining whether or not the maximum value Imax is a value equal to or greater than a predetermined threshold value Th1.

In a case where it is determined that the maximum value Imax is not saturated, the determination unit 34 calculates a ratio (I2/I1) between the first estimated value I1 and the second estimated value I2 as a correction coefficient H0 of the first estimated value I1. Then, the calculated correction coefficient H0 is stored in the storage 23.

In the present embodiment, each time the breast M is imaged, the determination unit 34 determines whether or not the maximum value Imax is saturated, calculates the correction coefficient H0 in a case where it is determined that the maximum value Imax is not saturated, and stores the calculated correction coefficient H0 in the storage 23.

On the other hand, in a case where it is determined that the maximum value Imax is saturated, the determination unit 34 calculates a representative value C0 of a predetermined number of correction coefficients with reference to the correction coefficient stored in the storage 23. In the present embodiment, the predetermined number is set to 1000 in order to use correction coefficients for the past 1000 cases with the latest correction coefficient as a reference. However, the predetermined number is not limited thereto. As the representative value C0, a statistical value such as an average value, a median value, a mode value, a maximum value, or a minimum value of a predetermined number of correction coefficients can be used.

The determination unit 34 corrects the first estimated value I1 with the calculated representative value C0 of the correction coefficient. Specifically, the first estimated value I1 is multiplied by the representative value C0. Then, the determination unit 34 determines the corrected first estimated value I1·C0 as the direct arrival dose Id used for calculation of the mammary gland content rate.

The calculation unit 35 calculates a mammary gland content rate R of the breast M based on a breast region arrival dose Im, which is an arrival dose of X-rays to the breast region A1 included in the breast image G0, and the direct arrival dose Id determined by the determination unit 34. Hereinafter, the calculation of the mammary gland content rate will be described. In the present embodiment, the mammary gland content rate is calculated by regarding the pixel value of each pixel of the breast region A1 in the breast image G0 as the breast region arrival dose Im.

Assuming that the thickness of the breast M corresponding to a certain pixel position in the breast image G0 is T and the ratio of the mammary gland to the thickness T, that is, the mammary gland content rate is R, the breast region arrival dose Im is expressed by the following Equation (2) using the direct arrival dose Id.

$$\log Im = \log Id - \mu f \cdot (1-R) \cdot T - \mu m \cdot R \cdot T \quad (2)$$

In Equation (2), the height of the compression plate 17 is used as the thickness T of the breast M. In the vicinity of the skin line that is not in contact with the compression plate 17 in the breast M, the thickness T of the breast M may be calculated from the height of the compression plate 17 by regarding the outline on the cross section in the thickness direction of the breast M as an arc. $\mu f$ is an attenuation coefficient of X-rays due to fat, and $\mu m$ is an attenuation coefficient of X-rays due to mammary gland. The values of the attenuation coefficients $\mu f$ and $\mu m$ are known, and are stored in the storage 23 in the present embodiment. Therefore, by modifying Equation (2), the mammary gland content rate R is calculated from the following Equation (3).

$$R = \frac{\log Id - \log I_m - \mu f \cdot T}{(\mu_m - \mu f) \cdot T} \quad (3)$$

Figure 6:
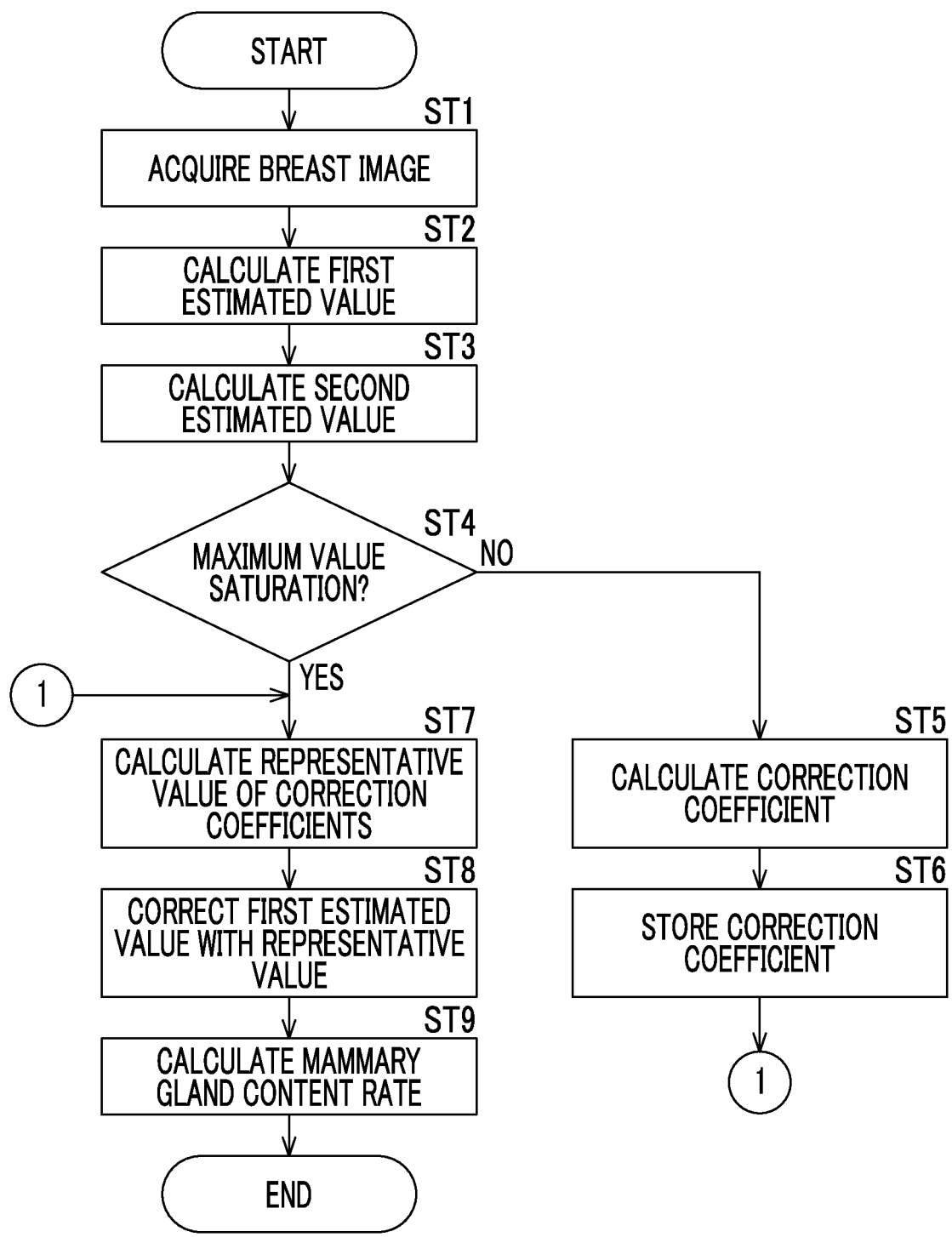
FIG. 6 is a flowchart showing a process performed in the present embodiment.

Next, a process performed in the present embodiment will be described. FIG. 6 is a flowchart showing the process performed in the present embodiment. First, the image acquisition unit 31 acquires the breast image G0 (step ST1), and the first estimation unit 32 calculates the first estimated value I1 of the direct arrival dose in the direct X-ray region, which is included in the breast image G0 and to which X-rays are directly emitted, based on the imaging conditions at the time of X-ray imaging (step ST2). Then, the second estimation unit 33 calculates the second estimated value I2 of the direct arrival dose based on the pixel value of the direct X-ray region A2 included in the breast image G0 (step ST3).

Then, the determination unit 34 determines whether or not the maximum value Imax of the pixel values in the analysis region A3, which has been calculated by the second estimation unit 33, is saturated (step ST4). In a case where it is determined that the maximum value Imax is not saturated (step ST4: NO), the determination unit 34 calculates the ratio (I2/I1) between the first estimated value I1 and the second estimated value I2 as the correction coefficient H0 of the first estimated value I1 (step ST5). Then, the determination unit 34 stores the correction coefficient H0 in the storage 23 (step ST6).

On the other hand, in a case where it is determined that the maximum value Imax is saturated (step ST4: YES), the determination unit 34 calculates the representative value C0 of a predetermined number of correction coefficients with reference to the correction coefficient stored in the storage 23 (step ST7). Then, the determination unit 34 corrects the first estimated value I1 with the representative value C0 of the correction coefficient (step ST8), and determines the corrected first estimated value I1·C0 as the direct arrival dose Id used for calculation of the mammary gland content rate. Then, the calculation unit 35 calculates the mammary gland content rate R using the direct arrival dose Id determined by the determination unit 34 (step ST9), and ends the process.

As described above, according to the present embodiment, the direct arrival dose Id is determined based on the first estimated value I1 and the second estimated value I2, and the mammary gland content rate R of the breast M is calculated based on the direct arrival dose Id and the breast region arrival dose Im that is the arrival dose to the breast region A1 included in the breast image G0. Therefore, the direct arrival dose Id can be determined by correcting the first estimated value I1 according to the case where the pixel value is saturated in the breast image G0 and the case where the imaging conditions at the time of imaging are changed. As a result, it is possible to accurately calculate the mammary gland content rate R regardless of saturation of the pixel value in the breast image G0 and changes in the imaging conditions at the time of imaging the breast.

In the embodiment described above, the determination unit 34 corrects the first estimated value I1 using the representative value C0 of the correction coefficient to determine the direct arrival dose Id. However, in a case where it is determined that the maximum value Imax is saturated, the determination unit 34 may determine the first estimated value I1 as the direct arrival dose Id used for calculation of the mammary gland content rate. In addition, in a case where it is determined that the maximum value Imax is not saturated, the determination unit 34 may determine the second estimated value I2 as the direct arrival dose Id used for calculation of the mammary gland content rate.

In the embodiment described above, in a case where it is determined that the maximum value Imax is not saturated, the first estimated value I1 may be corrected by multiplying the first estimated value I1 by the correction coefficient H0, and the corrected first estimated value I1·H0 may be determined as the direct arrival dose Id used for calculation of the mammary gland content rate. In this case, since the correction coefficient H0=I2/I1, the corrected first estimated value I1·H0 substantially matches the second estimated value I2.

Correcting the first estimated value I1 using the calculated correction coefficient H0 is equivalent to correcting the tables LUT1 and LUT2 using the correction coefficient H0. Therefore, in a case where it is determined that the maximum value Imax is not saturated, the determination unit 34 may correct the tables LUT 1 and LUT 2 using the correction coefficient H0. In this case, the first estimation unit 32 calculates the first estimated value I1 again with reference to the corrected tables LUT1 and LUT2. Then, the determination unit 34 determines the first estimated value I1, which has been calculated with reference to the corrected tables LUT1 and LUT2, as the direct arrival dose Id used for calculation of the mammary gland content rate.

Hereinafter, the effect of the present embodiment will be described.

It is determined whether or not the maximum value of the pixel values of the direct X-ray region included in the breast image is saturated. In a case where it is determined that the maximum value is not saturated, a ratio between the first estimated value and the second estimated value is calculated as a correction coefficient of the first estimated value, the first estimated value is corrected with the correction coefficient, and the corrected first estimated value is determined as a direct arrival dose. Therefore, even if the first estimated value changes due to changes in the imaging conditions, it is possible to determine the direct arrival dose by appropriately correcting the first estimated value using the relationship between the first estimated value and the second estimated value. As a result, it is possible to accurately calculate the mammary gland content rate regardless of saturation of the pixel value in the breast image and changes in the imaging conditions at the time of imaging the breast.

By storing correction coefficients, calculating the representative value of a predetermined number of stored correction coefficients, correcting the first estimated value using the representative value, and determining the corrected first estimated value as a direct arrival dose, it is possible to correct the first estimated value using the uniform correction coefficient.

It is determined whether or not the maximum value of the pixel values of the direct X-ray region included in the breast image is saturated. In a case where it is determined that the maximum value is saturated, the first estimated value is determined as a direct arrival dose used for calculation of the mammary gland content rate. In a case where it is determined that the maximum value is not saturated, the second estimated value is determined as a direct arrival dose used for calculation of the mammary gland content rate. Therefore, it is possible to determine the direct arrival dose by selecting the estimated value to be used according to the case where the pixel value is saturated in the breast image and the case where the imaging conditions at the time of imaging are changed. As a result, it is possible to accurately calculate the mammary gland content rate regardless of saturation of the pixel value in the breast image.

What is claimed is:

1. A mammary gland content rate calculation device, comprising:
    a processor that is configured to:
    acquire a breast image obtained by imaging a breast with X-rays, wherein the breast image is an image of the breast and a region around the breast;
    calculate a first estimated value of a direct arrival dose based on imaging conditions at a time of X-ray imaging, wherein the direct arrival dose is an X-ray dose that directly reaches the region around the breast;
    calculate a second estimated value of the direct arrival dose based on at least a portion of pixel values of a direct X-ray region, which corresponds to the region around the breast, included in the breast image;
    determine whether or not a maximum value of the pixel value of the direct X-ray region included in the breast image is saturated;
    determine a direct arrival dose, which is to be used for calculation of a mammary gland content rate, based on the first estimated value, the second estimated value, and a result of determining the direct arrival dose; and
    calculate the mammary gland content rate of the breast based on a breast region arrival dose, which is an arrival dose of X-rays to a region of the breast included in the breast image, and the determined direct arrival dose.

2. The mammary gland content rate calculation device according to claim 1,
    wherein the processor is configured to determine whether or not a maximum value of the pixel value of the direct X-ray region included in the breast image is saturated, and calculate a ratio between the first estimated value and the second estimated value as a correction coefficient of the first estimated value in a case where it is determined that the maximum value is not saturated.

3. The mammary gland content rate calculation device according to claim 2,
    wherein the processor is configured to correct the first estimated value with the correction coefficient, and determine a corrected first estimated value as a direct arrival dose to be used for calculation of the mammary gland content rate.

4. The mammary gland content rate calculation device according to claim 2, further comprising:
    a storage unit that stores the correction coefficient,
    wherein the processor is configured to calculate a representative value of a predetermined number of correction coefficients stored in the storage unit, correct the first estimated value with the representative value, and determine a corrected first estimated value as a direct arrival dose to be used for calculation of the mammary gland content rate.

5. The mammary gland content rate calculation device according to claim 1,
    wherein the processor is configured to determine whether or not a maximum value of the pixel value of the direct X-ray region included in the breast image is saturated, and determine the first estimated value as a direct arrival dose to be used for calculation of the mammary gland content rate in a case where it is determined that the maximum value is saturated and determines the second estimated value as a direct arrival dose to be used for calculation of the mammary gland content rate in a case where it is determined that the maximum value is not saturated.

6. The mammary gland content rate calculation device according to claim 1,
wherein the processor is configured to acquire a dose rate and a sensitivity of a radiation detector, which acquires the breast image, based on the imaging conditions, and calculate the first estimated value using an X-ray dose at the time of the X-ray imaging, the dose rate, and the sensitivity of the radiation detector.

7. The mammary gland content rate calculation device according to claim 6,
wherein, for each type of target/filter and a tube voltage in an X-ray source used at the time of the X-ray imaging, the processor is configured to acquire the dose rate and the sensitivity of the radiation detector with reference to a table in which values of the dose rate and the sensitivity of the radiation detector are set.

8. A mammary gland content rate calculation method, comprising:
acquiring a breast image obtained by imaging a breast with X-rays, wherein the breast image is an image of the breast and a region around the breast;
calculating a first estimated value of a direct arrival dose based on imaging conditions at a time of X-ray imaging, wherein the direct arrival dose is an X-ray dose that arrives directly at the region around the breast;
calculating a second estimated value of the direct arrival dose based on at least a portion of pixel values of a direct X-ray region, which corresponds to the region around the breast, included in the breast image;
determining whether or not a maximum value of the pixel value of the direct X-ray region included in the breast image is saturated;
determining a direct arrival dose, which is to be used for calculation of a mammary gland content rate, based on the first estimated value, the second estimated value, and a result of determining the direct arrival dose; and
calculating the mammary gland content rate of the breast based on a breast region arrival dose, which is an arrival dose of X-rays to a region of the breast included in the breast image, and the determined direct arrival dose.

9. A non-transitory computer-readable storage medium that stores a mammary gland content rate calculation program causing a computer to execute:
a step of acquiring a breast image obtained by imaging a breast with X-rays, wherein the breast image is an image of the breast and a region around the breast;
a step of calculating a first estimated value of a direct arrival dose based on imaging conditions at a time of X-ray imaging, wherein the direct arrival dose is an X-ray dose that arrives directly at the region around the breast;
a step of calculating a second estimated value of the direct arrival dose based on at least a part of pixel values of a direct X-ray region, which corresponds to the region around the breast, included in the breast image;
a step of determining whether or not a maximum value of the pixel value of the direct X-ray region included in the breast image is saturated;
a step of determining a direct arrival dose, which is to be used for calculation of a mammary gland content rate, based on the first estimated value, the second estimated value, and a result of determining the direct arrival dose; and
a step of calculating the mammary gland content rate of the breast based on a breast region arrival dose, which is an arrival dose of X-rays to a region of the breast included in the breast image, and the determined direct arrival dose.

* * * * *